(12) United States Patent
Speier et al.

(10) Patent No.: US 7,606,611 B2
(45) Date of Patent: Oct. 20, 2009

(54) METHOD AND APPARATUS FOR DETERMINING THE AZIMUTHAL ORIENTATION OF A MEDICAL INSTRUMENT FROM MR SIGNALS

(75) Inventors: Peter Speier, Erlangen (DE); Frank Wacker, Berlin (DE)

(73) Assignee: Siemens Aktiengesellschaft, Munich (DE)

( * ) Notice: Subject to any disclaimer, the term of this patent is extended or adjusted under 35 U.S.C. 154(b) by 604 days.

(21) Appl. No.: 11/190,090

(22) Filed: Jul. 26, 2005

(65) Prior Publication Data

US 2006/0025678 A1 Feb. 2, 2006

(30) Foreign Application Priority Data

Jul. 26, 2004 (DE) .................. 10 2004 036 217

(51) Int. Cl.
*A61B 5/05* (2006.01)
(52) U.S. Cl. .............. 600/410; 600/407; 600/420; 600/421; 600/422; 600/423; 600/424
(58) Field of Classification Search .......... 600/423
See application file for complete search history.

(56) References Cited

U.S. PATENT DOCUMENTS

| | | | | |
|---|---|---|---|---|
| 5,303,707 A * | 4/1994 | Young | .................. | 600/423 |
| 5,307,808 A * | 5/1994 | Dumoulin et al. | ............ | 600/423 |
| 5,353,795 A * | 10/1994 | Souza et al. | ................ | 600/423 |
| 5,951,472 A * | 9/1999 | Van Vaals et al. | ............ | 600/411 |
| 5,964,705 A * | 10/1999 | Truwit et al. | ................ | 600/423 |
| 6,023,636 A * | 2/2000 | Wendt et al. | ................ | 600/410 |
| 6,122,538 A * | 9/2000 | Sliwa et al. | ................ | 600/407 |
| 6,216,026 B1 * | 4/2001 | Kuhn et al. | ................ | 600/409 |
| 6,272,370 B1 * | 8/2001 | Gillies et al. | ................ | 600/411 |
| 6,493,573 B1 * | 12/2002 | Martinelli et al. | ............ | 600/424 |
| 6,593,884 B1 * | 7/2003 | Gilboa et al. | ................ | 342/448 |
| 6,594,517 B1 * | 7/2003 | Nevo | .................. | 600/411 |
| 6,636,757 B1 * | 10/2003 | Jascob et al. | ................ | 600/424 |
| 6,687,530 B2 * | 2/2004 | Dumoulin | .................. | 600/423 |
| 6,690,963 B2 * | 2/2004 | Ben-Haim et al. | ............ | 600/424 |
| 2002/0055678 A1 * | 5/2002 | Scott et al. | .................. | 600/423 |
| 2002/0058868 A1 * | 5/2002 | Hoshino et al. | .............. | 600/423 |
| 2002/0115931 A1 * | 8/2002 | Strauss et al. | ................ | 600/420 |
| 2003/0114747 A1 * | 6/2003 | Smith | .................. | 600/420 |
| 2003/0117135 A1 * | 6/2003 | Martinelli et al. | ............ | 324/301 |
| 2003/0160721 A1 * | 8/2003 | Gilboa et al. | ................ | 342/450 |
| 2003/0216639 A1 * | 11/2003 | Gilboa et al. | ................ | 600/424 |
| 2004/0220470 A1 * | 11/2004 | Karmarkar et al. | .......... | 600/423 |
| 2005/0054913 A1 * | 3/2005 | Duerk et al. | ................ | 600/423 |
| 2005/0054914 A1 * | 3/2005 | Duerk et al. | ................ | 600/423 |
| 2005/0148864 A1 * | 7/2005 | Slade et al. | ................ | 600/423 |

(Continued)

FOREIGN PATENT DOCUMENTS

WO     WO 96/05768     2/1996

(Continued)

*Primary Examiner*—Brian Casler
*Assistant Examiner*—James Kish
(74) *Attorney, Agent, or Firm*—Schiff Hardin LLP

(57) ABSTRACT

A medical apparatus, includes a medical instrument with an acquisition unit for a magnetic resonance signal, the acquisition unit exhibiting a non-constant sensitivity profile in the azimuthal direction relative to an axis of the medical instrument. An azimuthal orientation of the medical apparatus is determined by an evaluation unit from magnetic resonance signals received by the acquisition unit.

18 Claims, 4 Drawing Sheets

U.S. PATENT DOCUMENTS

2005/0267359 A1* 12/2005 Hussaini et al. ............. 600/423
2006/0025677 A1* 2/2006 Verard et al. ................ 600/423
2006/0281988 A1* 12/2006 Weiss ......................... 600/423

FOREIGN PATENT DOCUMENTS

| WO | WO 96/05768 A1 * | 2/1996 |
| WO | WO 99/60370 | 11/1999 |
| WO | WO 00/10456 | 3/2000 |
| WO | WO 01/75465 | 10/2001 |
| WO | WO 01/75465 A1 * | 10/2001 |
| WO | WO 03/051192 | 6/2003 |

* cited by examiner

METHOD AND APPARATUS FOR DETERMINING THE AZIMUTHAL ORIENTATION OF A MEDICAL INSTRUMENT FROM MR SIGNALS

BACKGROUND OF THE INVENTION

1. Field of the Invention

The present invention concerns a method and apparatus for use with a magnetic resonance imaging apparatus, for determining the azimuthal orientation of a medical instrument from magnetic resonance (MR) signals.

2. Description of the Prior Art

For medical procedures involving in vivo insertion of a medical instrument, for example a catheter, monitoring of the position and alignment of the instrument is frequently necessary. To make placement of the catheter tip easier, the tip generally is formed with a bend. The catheter can thereby also be inserted into branched vessels. Whether the catheter reaches into a branch or passes by the branch depends on the rotation angle of the catheter around its own axis. This rotation angle in the following is designated as the azimuthal orientation. It is desirable to be able to determine the azimuthal orientation of the curved catheter tip during the procedure in order to make targeted placement in a vessel easier.

It is generally not possible to discern the orientation of the catheter at the insertion point in the body from the orientation of the catheter tip, since the catheter is not resistant to buckling or bending over its entire length.

One possibility for determining the azimuthal orientation of the catheter tip is to monitor using continuous fluoroscopic radiography. The azimuthal orientation of the catheter tip can be directly determined by this projection method. For this purpose, it is necessary to rotate the catheter, or to move the catheter forward and back, in order to detect the orientation. With radiographic observation, however, the vessel outlets into which the catheter should be inserted generally are not visible. For this reason, the catheter manipulation and probing place high demands on the experience of the treating physician and often require long radiography times, which is disadvantageous for the patient due to the x-ray dose associated therewith.

The position and alignment of the catheter or a guide wire connected thereto can be shown in a magnetic resonance image by means of magnetic resonance measurements. For this purpose, for example, the catheter can be equipped with coils for acquisition of a magnetic resonance signal. The position of the tip can be determined from the acquired signal by comparison with signals of the other coils that are used, for example, for images. The catheter is not necessarily directly shown in the magnetic resonance image, but the position of the catheter tip is superimposed in a magnetic resonance image of the surrounding vessels. The position of the catheter so acquired in this manner can be used to track the position of the catheter tip in real time by ensuring that the measurement slice in which the tip is currently located is always currently displayed so the position of the type always remains visible in the magnetic resonance image. It has not been possible, however, to also assess or to determine the azimuthal orientation of the catheter tip in real time with this known method.

The degree of the curvature of the tip depends on the size of the particular vessel in which the catheter is currently located. In narrow vessels, the tip is straightened by the pressure of the vessel walls, which reduces its degree of curvature in comparison with larger vessels in which the curvature is not altered. The significantly curved tip in large vessels can be shown in a magnetic resonance image. The actual curvature, and therewith the azimuthal orientation, however, can be detected only with difficulty even in high-resolution magnetic resonance images. In contrast to this, in narrow vessels the azimuthal orientation cannot be detected at all in the magnetic resonance image due to the straightened tip. Therefore it cannot to be seen in advance in which direction the catheter is bent immediately upon the vessel becoming wider again, or when the catheter arrives at a branch. A continuous representation of the azimuthal orientation of the tip during the entire procedure time thus has not been possible with magnetic resonance measurements.

SUMMARY OF THE INVENTION

An object of the present invention is to provide a medical apparatus and an operating method therefor that allow the azimuthal orientation of a medical instrument to be determined by means of magnetic resonance measurements.

This object is achieved by a medical apparatus with a medical instrument having an acquisition unit for acquiring a magnetic resonance signal that is firmly connected to the medical instrument and exhibits a non-constant (non-uniform) reception sensitivity profile in the azimuthal direction relative to an axis of the medical instrument. Furthermore, the medical apparatus has an evaluation unit that is connected with the acquisition unit and that determines the azimuthal orientation of the medical instrument from the magnetic resonance signal acquired by the acquisition unit. The azimuthal orientation of the instrument can always be determined from the measured magnetic resonance signals due to the non-constant sensitivity profile of the acquisition unit in the azimuthal direction and the fixed connection with the medical instrument. In the ideal case, the sensitivity profile is asymmetric, such that the azimuthal orientation of the tip can be unambiguously determined. Sensitivity profiles in which an ambiguity occurs, for example modulo 180°, can also be used. Even with this limitation, an efficient manipulation of the medical apparatus is possible since, in comparison to previous techniques, only two possibilities are available for selection and the correct orientation can quickly be found by testing. The information thus acquired about the azimuthal orientation of the medical instrument can be superimposed into an overview image of the surrounding anatomy of the patient in the planning (image preparation) for magnetic resonance measurements. Thus, for example, the vessels can be shown in the magnetic resonance image and, as is known, the position of the inserted medical instrument can be displayed. The azimuthal orientation of the medical apparatus can additionally be superimposed, so manipulation of the instrument is made easier for the physician. The use of magnetic resonance measurements for determination of the azimuthal orientation moreover has the advantage that the patient is exposed to no radiation load as occurs, for example, in radiography.

In a preferred embodiment, the acquisition unit has a half-open coaxial cable for acquisition of the magnetic resonance signal. The sensitivity profile is asymmetrical, such that magnetic resonance signals can be acquired only from a limited angle range in the azimuthal direction.

In a preferred embodiment, the medical instrument has a reference unit for acquisition of the magnetic resonance signal, the reference unit being connected with the evaluation unit. The sensitivity profile of the reference unit differs from the sensitivity profile of the acquisition unit in the azimuthal direction, at least in a limited range. An evaluation of the magnetic resonance measurement implemented with the acquisition unit is made easier by the reference measurement.

In a method according to the invention for determination of the azimuthal orientation, the magnetic resonance signal measured with the acquisition unit to the evaluation unit, which determines therefrom the azimuthal orientation dependent on the non-constant sensitivity profile.

In an embodiment the method, the magnetic resonance signal is acquired with the reference unit and is likewise supplied to the evaluation unit, which determines from this a non-azimuthal orientation of the axis of the medical instrument. For example, the orientation and position of the medical instrument can be determined, which is of great importance for accurate placement.

DESCRIPTION OF THE PREFERRED EMBODIMENTS

Figure 1:
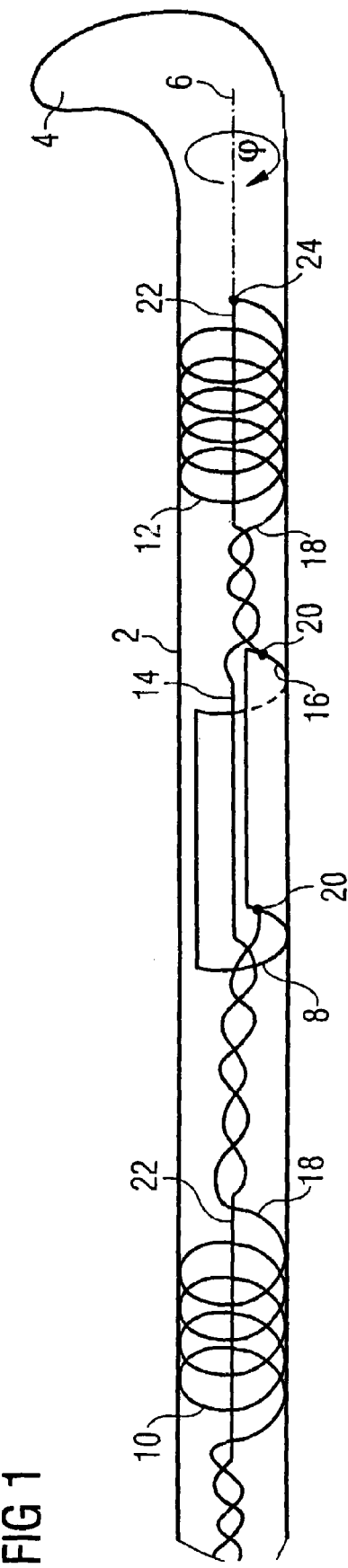
FIG. 1 is a schematic of a portion of a medical instrument in the embodiment of a catheter with an acquisition unit and a reference unit according to the invention.

FIG. 1 shows a section of a catheter 2 with a curved tip 4. The azimuthal orientation of a tip 4 is designated by the angle φ, which is defined relative to the catheter axis 6. The catheter 2 has an acquisition unit, which in this embodiment is a half-open coaxial cable 8, and a reference unit formed by two coils 10 and 12. The axes of symmetry of the coils 10 and 12 and of the coaxial cable 8 coincide with the catheter axis 6. The catheter 2 is resistant to buckling over its entire length, i.e. the coaxial cable 8, both coils 10 and 12 and the tip 4 are in a fixed alignment relative to one another in the azimuthal direction. The coaxial cable 8 is connected in series with the coils 10 and 12, with the coaxial cable 8 between the coils 10 and 12. The distance of the coaxial cable 8 from the coil 10 is thereby larger than the distance to the coil 12. An asymmetry is thereby created in the arrangement from which the orientation of the catheter axis 6 can be determined, as explained below using FIG. 2. The coaxial cable 8 has an inner conductor 14 that runs along the catheter axis 6 and an outer conductor 16 partially shielding the inner conductor 14. The outer conductor 16 has the shape of a cylinder cut in half parallel to its axis of symmetry, the cylinder likewise being aligned parallel to the catheter axis 6. The coils 10 and 12 are formed by windings of two cables 18 that are connected with the outer conductor 16 of the coaxial cable 8 at two contact points 20. The inner conductor 14 of the coaxial cable 8 is continued beyond the outer conductor 16 and crosses both coils 10 and 12 along their axes of symmetry 22. Furthermore, the inner conductor is connected with the cable 18 at a contact point 24 near the tip 4 of the catheter 2, such that a circuit is created.

When the catheter 2 is located in a patient in an MR scanner 63 (See FIG. 7), magnetic resonance signals can be acquired with the coaxial cable 8 and the coils 10 and 12 and supplied via a cable 65 (connected at the left end of the catheter 4 shown in FIG. 1) to an evaluation unit 64. A spatial variation of the magnetic field strength, and with it a variation of the Larmor frequency, is set by the magnetic field gradients used in magnetic resonance examinations. Signals at respectively different frequencies are therefore detected (received) by the coaxial cable 8 and the coils 10 and 12, dependent on the respective reception sensitivity profile. The evaluation unit 64 can resolve these signal components at different frequencies by spectral analysis, for example. The orientation of the catheter axis 6 and the position of the tip 4 can be determined from those signals and shown in a magnetic resonance image acquired in a known manner with a local coil located outside of the patient.

Figure 2:
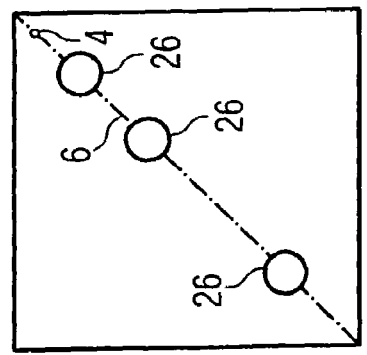
FIG. 2 schematically illustrates the signals of the acquisition unit and the reference unit in the plane of a magnetic resonance image.

FIG. 2 shows the orientation of the coaxial cable 8 and of both coils 10 and 12 from FIG. 1 using the positions 26 of the respective magnetic resonance signals acquired with them. Since the spacings between the coaxial cable 8 and both coils 10 and 12 are of different sizes, the orientation of the catheter axis 6 and of the tip 4 can be determined.

Figure 3:
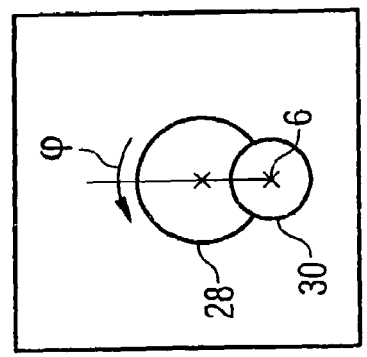
FIG. 3 schematically illustrates the sensitivity profile of the half-open coaxial cable used as the acquisition unit in the embodiment.

In a schematic representation, FIG. 3 shows the reception sensitivity profile 28 of the coaxial cable 8 and the reception sensitivity profile 30 of both coils 10 and 12 from FIG. 1 in a plane perpendicular to the catheter axis 6. While the sensitivity profiles 30 of the coils 10 and 12 are symmetrical around the catheter axis 6, due to the half-open shielding the sensitivity profile 28 of the coaxial cable 8 exhibits an asymmetry so that it is only sensitive to magnetic resonance signals from the direction of the open side. An unambiguous indication of the azimuthal orientation of the tip for guidance of the catheter 4 is established by the fixed azimuthal position of the coaxial cable 8 relative to the tip.

Figure 4:
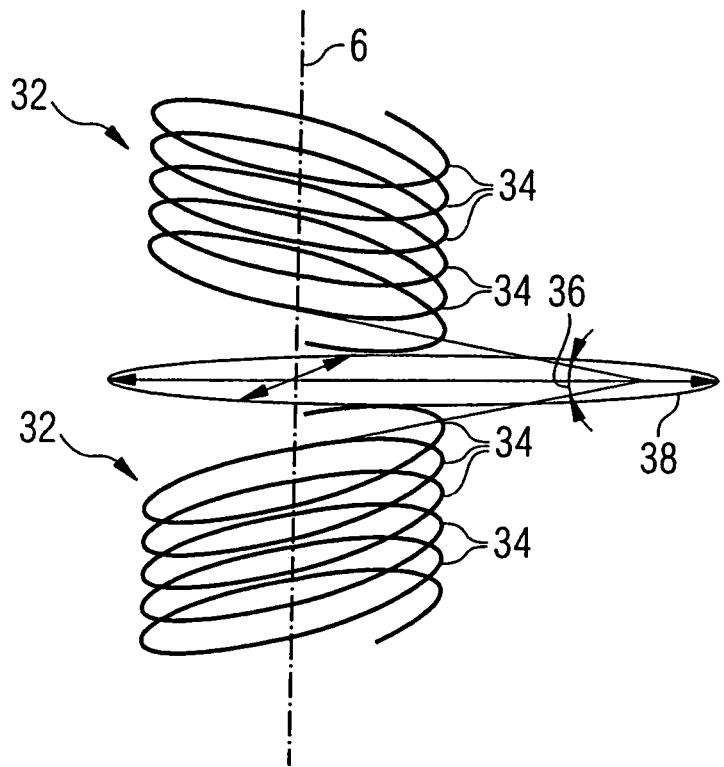
FIG. 4 schematically illustrates a further embodiment of the acquisition unit, as a tilted dipole coil.

In a second exemplary embodiment, a tilted dipole coil is fixed to the catheter 4 as an acquisition unit instead of the half-open coaxial cable 8 of FIG. 1. Since the remaining design is identical to that shown in FIG. 1, FIG. 4 shows only the tilted dipole coil and the catheter axis 6. The titled dipole coil is composed of two coil parts 32 with windings 34 wound at an angle, the windings 34 of both coil parts 32 being tilted opposite to one another at an angle 36. An asymmetry of the sensitivity profile of the dipole coil results from this arrangement, which is represented by the sensitivity profile amplitude line 38 being off-center relative to the axis 6. The azimuthal orientation of the tip of the catheter can be determined by means of the dipole coil in a manner analogous to the exemplary embodiment described in FIG. 1.

Both of the aforementioned exemplary embodiments detect the intensity of the magnetic resonance signal, it is also possible to use the phase of the magnetic resonance signal to determine the azimuthal orientation. It is thereby necessary to eliminate possible phase shifts due to signal delays in the cables as well as frequency- and position-dependent phases, by calibration. As in the exemplary embodiments explained above, it is necessary to determine the azimuthal orientation of the catheter axis and its position.

Figure 5:
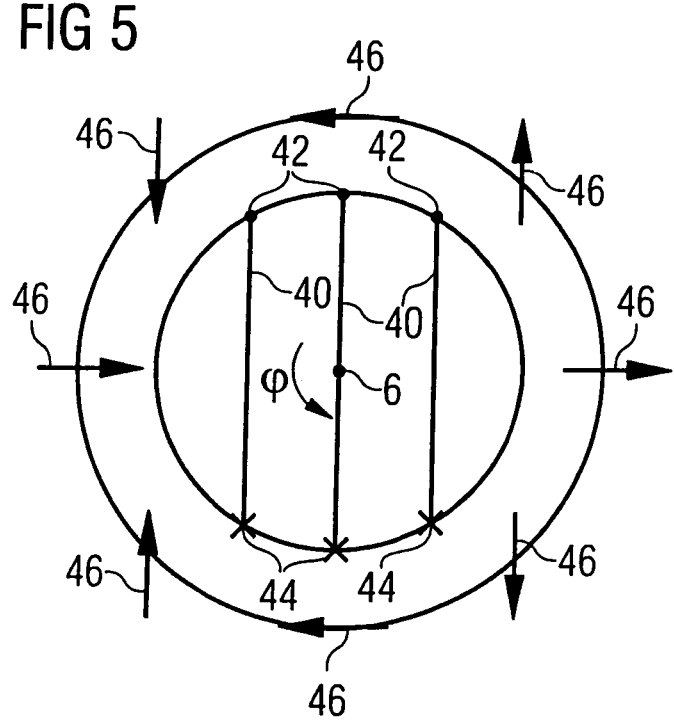
FIG. 5 schematically illustrates another embodiment of the acquisition unit, as a transversal dipole coil.

FIG. 5 shows a section through a transversal dipole coil that is formed by three conductor loops 40. The conductor loops 40 are perpendicular to the drawing plane, and exit the drawing plane at points 24 and re-enter into the drawings plane at crosses 44. The catheter axis 6 likewise is perpendicular to the drawing plane and thus is parallel to the conductor loops 40 of the transversal dipole coil. In a manner analogous to the exemplary embodiment in FIG. 1, the dipole coil is fixed at the catheter 4 so that the relative orientation of the dipole coil and the tip of the catheter is also fixed. The azimuthal orientation is again represented by the angle φ. The phase of the magnetic resonance signal in the environment of the dipole coil is represented by arrows 46, as an example. Given a half-rotation around the catheter axis 6, the phase completely rotates once, i.e. the phase is identical at two opposite sides of the dipole coil. The phase changes linearly with the azimuthal orientation φ. By analysis of the magnetic resonance signal acquired with the transversal dipole coil, the orientation of the dipole coil can be determined from the linear relation of the phase to the azimuthal angle, from which in turn the azimuthal orientation of the tip of the catheter can be determined. The determination of the azimuthal orientation is in this case established as modulo 180°. The ambiguity can be resolved by testing of the two different orientations. A different possibility to prevent this ambiguity is to use an asymmetrically-wound transversal dipole coil in which the conductor loops 40 are closer together on one side than on the other side. The phase then no longer changes linearly with the azimuthal angle and is thus unambiguously established.

Figure 6:
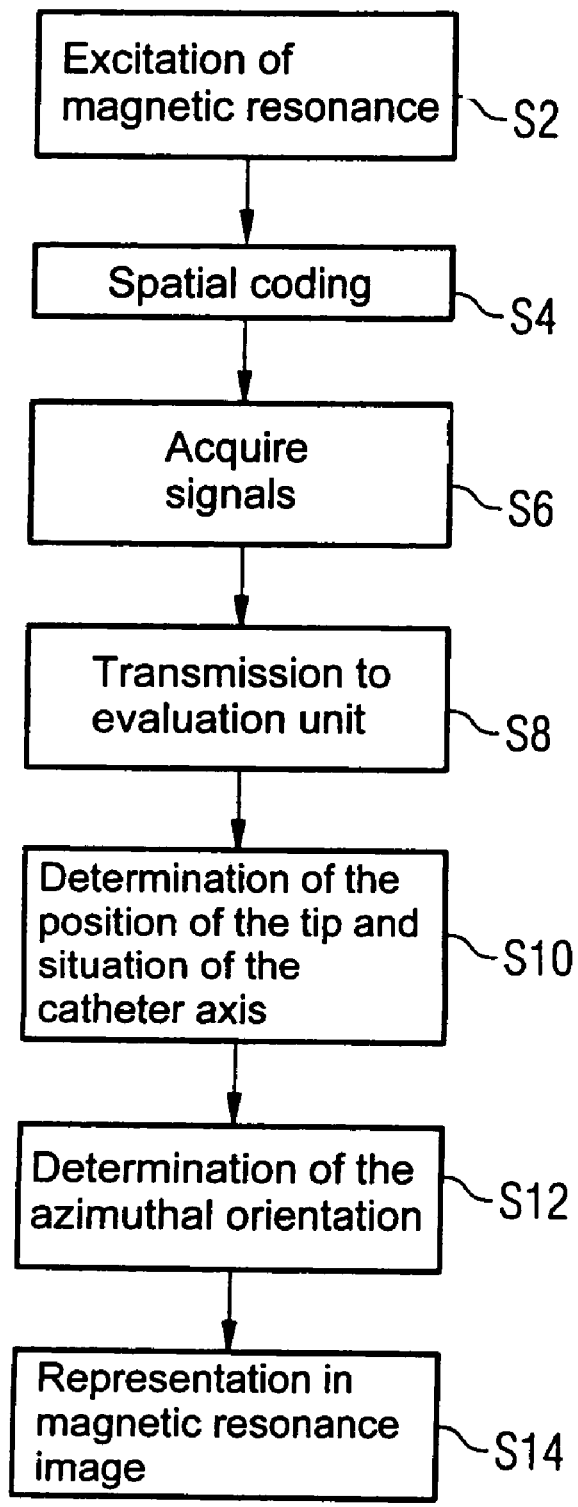
FIG. 6 is a flowchart of the inventive method for determination of the orientation of the medical instrument.

In the flowchart shown in FIG. 6 of an embodiment of the inventive method for determination of the azimuthal orientation, magnetic resonance is excited in a step S2. In a second step S4, a spatial coding is effected by means of gradient fields. In a subsequently-implemented step S6, the magnetic resonance signals are acquired with the acquisition unit and the reference unit. In a step S8, the corresponding measurement values are transmitted to the evaluation unit 64. In a step S10, the position of the catheter tip and the orientation of the catheter axis are initially determined from these measurement values. In a step S12, the azimuthal orientation of the catheter tip is determined. The determined azimuthal orientation and the position of the catheter tip, as well as the orientation of the catheter axis, are subsequently shown in a magnetic resonance image in a step S14.

Figure 7:
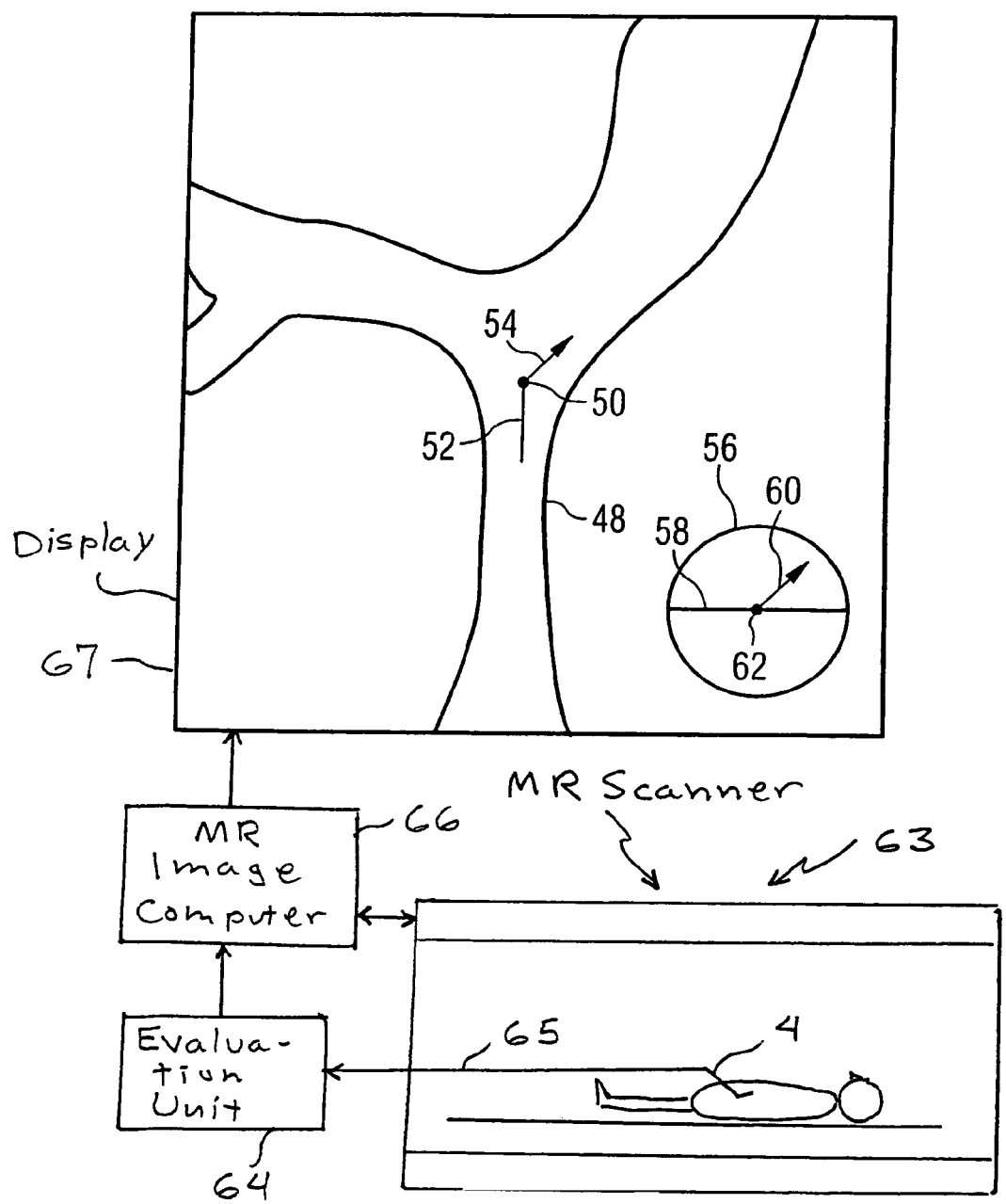
FIG. 7 schematically illustrates an MR apparatus embodying the inventive apparatus, showing a magnetic resonance image for explaining the invention.

FIG. 7 schematically shows a magnetic resonance image of a branched vessel 48, obtained in a known manner, in which information is obtained in accordance with the invention also is displayed. The magnetic resonance image shown in FIG. 7 (except for the instrument orientation information obtained in accordance with the invention) is acquired in a known manner, using the magnetic resonance scanner 63 to acquire magnetic resonance imaging data, that are supplied to a magnetic resonance image computer 66. The signals acquired from the catheter 4, in the manner described above, are supplied via a cable 65 to the evaluation unit 64, which supplies the orientation information to the magnetic resonance image computer 66 for inclusion in the magnetic resonance image that is presented at a display 67.

A point 50 that shows the position of the catheter tip is superimposed in the magnetic resonance image. A line 52 indicating the orientation of the catheter axis 6 is shown originating from the point 50. An arrow 54 that indicates the azimuthal orientation of the curved tip of the catheter 4 likewise originates from the point 50. The azimuthal orientation cannot be unambiguously indicated with the arrow 54. The arrow 54 can only indicate a projection of the tip of the catheter 4 on the image plane. If the tip does not lie in the image plane, it is necessary for the physician to rotate the catheter 4 so that the tip lies in the image plane and can be inserted into the branching vessel. A cross 56 that unambiguously indicates the azimuthal orientation of the tip is superimposed into the image as an orientation aid for the physician. A line 58 indicates the position of the image plane and an arrow 60 indicates the orientation of the tip. The catheter axis 6 is perpendicular to the display plane, which is illustrated by the point 62. The representation of the arrow 60 is selected as it would appear looking along the catheter axis 6 toward the tip. The physician thus knows at any point in time in which direction he or she must rotate the catheter 4 so that the tip arrives in the image plane. As an additional or alternative orientation aid, the arrow 54 can assume various colors, which cannot be shown in FIG. 7. A green arrow 54 can indicate that the tip lies in the image plane. If the tip has not yet reached the image plane, the arrow 54 can be red; if the tip is beyond the image plane, the arrow can be yellow.

Upon movement of the catheter 4, the slice used for acquisition of the magnetic resonance image is automatically guided along using the coils fastened to the catheter 4 so that an efficient and easy placement of the tip of the catheter 4 is possible.

Although modifications and changes may be suggested by those skilled in the art, it is the intention of the inventors to embody within the patent warranted hereon all changes and modifications as reasonably and properly come within the scope of their contribution to the art.

We claim:

1. A medical apparatus, for use with a magnetic resonance imaging system that generates a magnetic resonance image from magnetic resonance signals in an imaging volume, said medical apparatus comprising:
   a medical instrument configured for introduction into said imaging volume, said medical instrument having a longitudinal axis and said medical instrument being non-rotationally symmetric around said longitudinal axis;
   an acquisition unit attached in a fixed physical relation to said medical instrument, said acquisition unit having a reception sensitivity profile for said magnetic resonance signals that is non-constant in a plane substantially perpendicular to said longitudinal axis, and said acquisition unit receiving said magnetic resonance signals in said imaging volume and generating an output signal therefrom; and
   an evaluation unit in communication with said acquisition unit and supplied with said output signal from said acquisition unit, said evaluation unit being configured to electronically determine from the magnetic resonance signal received by said acquisition unit, a rotational orientation of said medical instrument in said plane, around said longitudinal axis, by identifying said rotational orientation due to said sensitivity profile being non-constant in said plane.

2. A medical apparatus as claimed in claim 1 wherein said acquisition unit has a reception sensitivity profile that is non-constant in the azimuthal direction relative to a phase of said magnetic resonance signal.

3. A medical apparatus as claimed in claim 1 wherein said acquisition unit has a reception sensitivity profile that is non-constant in the azimuthal direction relative to an intensity of said magnetic resonance signal.

4. A medical apparatus as claimed in claim 1 wherein said acquisition unit comprises a co-axial cable having a cable shielding with an opening therein.

5. A medical apparatus as claimed in claim 4 wherein said shielding has a circumference, and wherein said opening comprises approximately one-half of said circumference.

6. A medical apparatus as claimed in claim 1 wherein said acquisition unit comprises a coil arrangement.

7. A medical apparatus as claimed in claim 6 wherein said coil arrangement comprises a dipole coil having two windings each tilted with respect to said axis.

8. A medical apparatus as claimed in claim 6 wherein said coil arrangement comprises a transversal dipole coil.

9. A medical apparatus as claimed in claim 1 wherein said medical instrument comprises a reference unit that also receives said magnetic resonance signal, said reference unit having a reception sensitivity profile differing from the reception sensitivity profile of said acquisition unit in at least a range of said azimuthal direction.

10. A medical apparatus as claimed in claim 9 wherein said reference unit comprises at least one coil.

11. A medical apparatus as claimed in claim 10 wherein said coil has a constant reception sensitivity profile in said azimuthal direction.

12. A medical apparatus as claimed in claim 9 wherein said reference unit comprises a first coil and a second coil, said first coil being disposed at a different spacing along said axis from said acquisition unit than said second coil.

13. A medical apparatus as claimed in claim 1 wherein said medical instrument is a catheter.

14. A medical apparatus as claimed in claim 13 wherein said catheter has a catheter tip that is angled relative to said axis.

15. A method for determining the azimuthal orientation of a medical instrument, comprising the steps of:
introducing a medical instrument into an imaging region of a magnetic resonance imaging system, said medical instrument having a longitudinal axis, said medical instrument being non-rotationally symmetric around said longitudinal axis, and said medical instrument carrying an acquisition unit in fixed relation relative to said axis, said acquisition unit having a reception sensitivity profile for said magnetic resonance signals that is non-constant in a plane substantially perpendicular to said longitudinal axis;
detecting said magnetic resonance signals with said acquisition unit in generating an output signal therefrom; and
from said output signal, electronically determining a rotational orientation of said medical instrument in said plane, around said longitudinal axis, dependent on said reception sensitivity profile of said acquisition unit being non-constant in said plane.

16. A method as claimed in claim 15 wherein said instrument further comprises a reference unit in a fixed spatial relation to said acquisition unit, and comprising the additional steps of:
detecting said magnetic resonance signals with said reference unit and generating a reference signal therefrom; and
from said reference signal and said output signal, electronically determining a position and a non-azimuthal orientation of said axis of said instrument.

17. A method as claimed in claim 15 comprising electronically analyzing a phase of said output signal to determine the azimuthal orientation of the medical instrument.

18. A method as claimed in claim 15 comprising electronically analyzing an intensity of said output signal to determine the azimuthal orientation of the medical instrument.

* * * * *